(12) United States Patent
Nishitani et al.

(10) Patent No.: US 9,029,626 B2
(45) Date of Patent: May 12, 2015

(54) ABSORBENT ARTICLE

(75) Inventors: Kazuya Nishitani, Kagawa (JP);
Toshihisa Hayashi, Kagawa (JP);
Minako Sagisaka, Kagawa (JP)

(73) Assignee: Unicharm Corporation, Ehime (JP)

( * ) Notice: Subject to any disclaimer, the term of this patent is extended or adjusted under 35 U.S.C. 154(b) by 813 days.

(21) Appl. No.: 13/263,737

(22) PCT Filed: Apr. 7, 2010

(86) PCT No.: PCT/JP2010/056311
§ 371 (c)(1),
(2), (4) Date: Dec. 28, 2011

(87) PCT Pub. No.: WO2010/117015
PCT Pub. Date: Oct. 14, 2010

(65) Prior Publication Data
US 2012/0095425 A1 Apr. 19, 2012

(30) Foreign Application Priority Data
Apr. 10, 2009 (JP) ................................. 2009-096525

(51) Int. Cl.
*A61F 13/15* (2006.01)
*A61F 13/20* (2006.01)
(Continued)

(52) U.S. Cl.
CPC ....... *A61F 13/4704* (2013.01); *A61F 13/47218* (2013.01)

(58) Field of Classification Search
CPC ............ A61F 2013/15373; A61F 2013/15382; A61F 13/533
USPC ....... 604/378–380, 385.01, 385.101
See application file for complete search history.

(56) References Cited

U.S. PATENT DOCUMENTS 7,122,713 B2 10/2006 Komatsu et al.
2004/0176734 A1* 9/2004 Rasmussen et al. .......... 604/380
(Continued)

FOREIGN PATENT DOCUMENTS

EP 0876810 A2 11/1998
JP 2002238948 A 8/2002
(Continued)

OTHER PUBLICATIONS

Office Action issued Feb. 26, 2013 in counterpart Chinese Patent Application No. 201080015967.7.
(Continued)

*Primary Examiner* — Michele M Kidwell
(74) *Attorney, Agent, or Firm* — Lowe Hauptman & Ham, LLP

(57) ABSTRACT

An absorbent article includes a first curved portion and a second curved portion formed on the surface of a topsheet along a longitudinal direction of the absorbent article. The first curved portion is arranged in one pair to be symmetrical to a centerline of the absorbent article in a region in which the contact region is included, the region being an inside region more than each side part in a widthwise direction of the absorbent article, and is formed along a longitudinal direction of the absorbent article. The second curved portion is arranged in one pair in a region in which the contact region is included, the region being an inside region in the widthwise direction of the absorbent article more than the first curved portion, and is formed along the longitudinal direction of the absorbent article. The first curved portion and the second curved portion has a convex shape outward in the widthwise direction of the absorbent article, in the region in which the contact region is included.

2 Claims, 6 Drawing Sheets

(51) Int. Cl.
*A61F 13/533* (2006.01)
*A61F 13/47* (2006.01)
*A61F 13/472* (2006.01)

(56) References Cited

U.S. PATENT DOCUMENTS

| | | | |
|---|---|---|---|
| 2006/0116653 A1 | 6/2006 | Munakata et al. | |
| 2006/0276767 A1 | 12/2006 | Ueminami et al. | |
| 2011/0092944 A1* | 4/2011 | Sagisaka et al. | 604/385.101 |

FOREIGN PATENT DOCUMENTS

| | | |
|---|---|---|
| JP | 2006326299 A | 12/2006 |
| JP | 200789906 A | 4/2007 |
| JP | 2007125181 A | 5/2007 |
| JP | 2008110201 A | 5/2008 |
| JP | 2008541943 A | 11/2008 |
| JP | 2009000351 A | 1/2009 |
| JP | 2010136972 A | 6/2010 |
| JP | 2010136973 A | 6/2010 |
| WO | 2010071000 A1 | 6/2010 |

OTHER PUBLICATIONS

Search Report issued Mar. 8, 2013 in counterpart EP patent Application No. 10761714.4.
Office Action mailed Apr. 23, 2013 corresponds to Japanese patent application No. 2009-096525.
Office Action mailed Jan. 7, 2014, corresponds to Japanese patent application No. 2009-096525.
International Search Report for International Application No. PCT/JP2010/056311, mailed on Jul. 13, 2010.
Office Action dated Oct. 28, 2013, corresponds to Chinese patent application No. 201080015967.7.

* cited by examiner

ABSORBENT ARTICLE

RELATED APPLICATIONS

The present application is a National Phase of International Application No. PCT/JP2010/056311, filed Apr. 7, 2010 and claims priority from, Japanese Application No. 2009-096525, filed Apr. 10, 2009.

TECHNICAL FIELD

The present invention relates to an absorbent article having a topsheet, a backsheet, and an absorber.

BACKGROUND ART

Conventionally, in an absorbent article such as a sanitary napkins, there is proposed that a groove is provided on a surface of a topsheet in order to improve fitting property between a wearer's skin and the absorbent article (refer to Patent Document 1). In Patent Document 1, the shape of a groove is formed in a concave shape outward in a widthwise direction of the absorbent article. In the conventional absorbent article, a concave portion of the groove becomes fitted with the shape of a femoral part of a wearer, and a middle part of an absorber is intended to be lifted in a direction in which the middle part approaches a excretion part of the wearer by means of a compression force acting in a widthwise direction of the absorbent article from the femoral part of the wearer.

However, the conventional absorbent article mentioned above has entailed the following problem. That is, the shape of the groove is formed in the concave shape outward in the widthwise direction of the absorbent article. Therefore, in order to deform the shape in the widthwise direction of the absorbent article so that the middle part of the absorber is lifted in the direction in which the middle part approaches the excretion part of the wearer, a displacement is needed to an extent such that the middle part is pushed inward in the widthwise direction up to the vicinity of a top that is present innermost in the widthwise direction of the concave portion of the groove.

Therefore, there has been a problem that a lifting effect of lifting the middle part of the absorber in a direction in which the middle part approaches the excretion part is not sufficiently achieved depending on the bodyline of a wearer or the shape or the like of underwear on which the absorbent article is to be worn. In addition, in a use state, that is, in a state in which the absorbent article is compressed in a widthwise direction of the absorbent article by the femoral part, an absorption surface middle part of the absorber is displaced, and thus, an absorption area has been sometimes decreased.

PRIOR ART LITERATURE

Patent Document

Patent Document 1: JP-A-2002-238948 (Page 3, FIG. 1, and FIG. 3)

SUMMARY OF INVENTION

An absorbent article includes a topsheet having a contact surface which comes into contact with a skin of a wearer; a liquid-impermeable backsheet which does not permeate a liquid; and an absorber which is arranged between the topsheet and the backsheet, the absorbent article including a first curved portion and a second curved portion that are formed to be thinner than a thickness of the absorbent article in a contact region in which an excretion part of the wearer and the topsheet come into contact with each other. The first curved portion is arranged in one pair to be symmetrical to a centerline of the absorbent article in a region in which the contact region is included, the region being an inside region more than each side part in a widthwise direction of the absorbent article, and is formed along a longitudinal direction of the absorbent article, the second curved portion is arranged in one pair in a region in which the contact region is included, the region being an inside region in the widthwise direction of the absorbent article more than the first curved portion, and is formed along the longitudinal direction of the absorbent article, and the first curved portion and the second curved portion has a convex shape outward in the widthwise direction of the absorbent article, in the region in which the contact region is included.

BEST MODE FOR CARRYING OUT THE INVENTION

Figure 1:
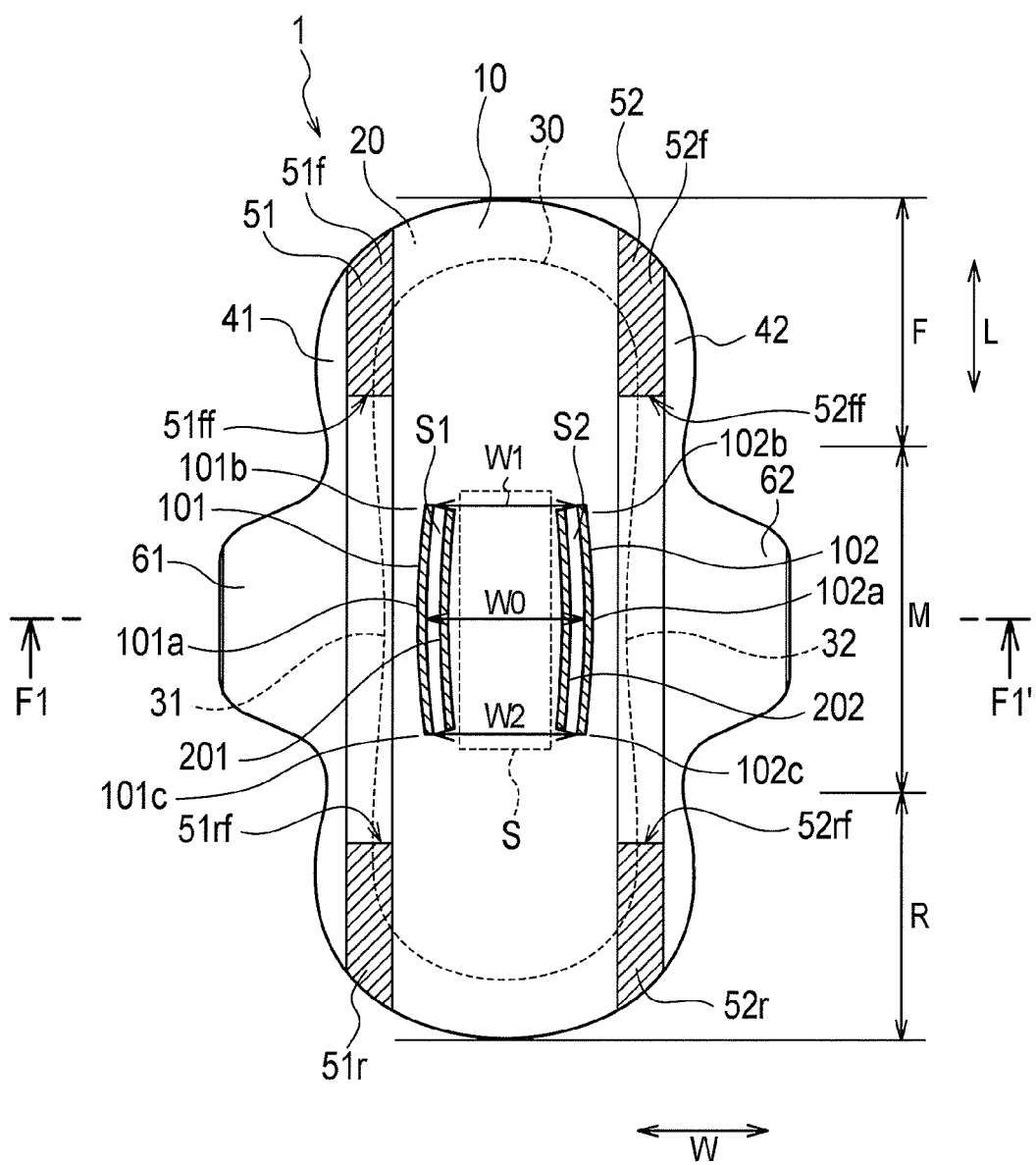
FIG. 1 is a plan view of an absorbent article according to a first embodiment.

An absorbent article according to each of the embodiments will be described with reference to the drawings. In the following description of the drawings, same or similar constituent elements are designated by same or similar reference numerals. However, it should be kept in mind that the drawings are merely schematic, and rates or the like of each dimension are different from actual ones. Therefore, specific dimensions or the like should be determined in consideration of the following description. In addition, of course, constituent elements with their different dimensional interrelationships or ratios are included in the respective drawings.

(First Embodiment)

An absorbent article according to a first embodiment will be described with reference to FIG. 1. FIG. 1 is a plan view of an absorbent article 1 according to the embodiment.

The absorbent article 1 in FIG. 1 is a sanitary napkin, for example. As shown in FIG. 1, the absorbent article 1 has a forward region F, a middle region M, and a rearward region R. The forward region F comes into contact a skin surface at a belly side of a wearer. The middle region M comes into contact a skin surface in the vicinity of a vaginal opening of the wearer. The rearward region R comes into contact a skin surface at a hip side of the wearer.

The absorbent article 1 has: a topsheet 10 which comes into contact with a wearer's skin; a liquid-impermeable backsheet 20 which does not permeate a liquid; and an absorber 30. The absorber 30 is arranged between the topsheet 10 and the backsheet 20. Therefore, the absorber 30 is indicated by the dotted line in FIG. 1. The absorber 30 is arranged at a middle portion in a longitudinal direction of the absorbent article 1.

In addition, the absorbent article 1 has side sheets 41 and 42 that are provided outside in a widthwise direction W of the absorber 30, which is orthogonal to a longitudinal direction L of the absorbent article 1. The absorbent article 1 has: a leakage prevention units (hereinafter, referred to as a "gathers") 51 and 52; and wing portions 61 and 62.

Although not shown in FIG. 1, a second sheet 11 may be provided between the topsheet 10 and the absorber 30.

It is preferable that dimensions in a longitudinal direction of the absorbent article 1 be within the range of 100 mm to 500 mm, and specifically, it is further preferable that the dimensions be within the range of 150 mm to 420 mm. In addition, it is preferable that dimensions in a widthwise direction be within the range of 30 mm to 200 mm, and specifically, it is preferable that the dimensions be within the range of 40 mm to 180 mm The topsheet 10 has a length which is substantially equal to that of the backsheet 20. The shape of an end part in a longitudinal direction of the topsheet 10 is substantially identical to that of an end part in a longitudinal direction of the backsheet 20. The top sheet 10 covers at least a surface of the absorber 30.

The topsheet 10 will be specifically described.

In the embodiment, the topsheet 10 is a nonwoven cloth. A material for the topsheet 10 is not limitative in particular, as long as it is a sheet-like material of its structure of permeating a liquid, such as a woven cloth or a pored plastic sheet. As a material for a woven cloth or a nonwoven cloth, either of a natural fiber and a chemical fiber can be used.

As examples of natural fibers, there are exemplified celluloses such as ground pulp or cotton. As examples of chemical fibers, there are exemplified: reproducible celluloses such as rayon or fibril rayon; semisynthetic celluloses such as acetate or triacetate; thermoplastic hydrophobic chemical fibers; or thermoplastic hydrophobic chemical fibers or the like to which hydrophilic treatment is applied.

As examples of thermoplastic hydrophobic chemical fibers, there are exemplified: single fibers such as polyethylene (PE), polypropylene (PP), or polyethylene terephthalate (PET); fibers made of graft polymerization of polyethylene and polypropylene; and composite fibers of core-clad structure or the like.

As a web forming method of a nonwoven cloth, there can be employed any one of a dry type (such as a card technique, a spunbond technique, a melt blown technique, or an air-raid technique) and a wet type. Among the dry type technique and the wet type technique, a plurality of methods may be combined. In addition, a method such as thermal bonding, needle punching, or chemical bonding is exemplified. A method of producing nonwoven cloth is not limitative to the abovementioned methods.

Further, a spun lace that is formed in a sheet shape by means of a water tangling technique can also be employed for the topsheet 10. Furthermore, nonwoven cloth having irregularities on a top layer side of the nonwoven cloth or an irregular nonwoven cloth obtained by providing total weight non-uniformity on the nonwoven cloth by applying air at the time of forming webs can also be employed for the topsheet 10. By forming irregularities on a surface, it is possible to alleviate a body fluid from dispersing along a surface of the topsheet 10 before penetrating the topsheet 10.

Next, the backsheet 20 will be specifically described.

In the embodiment, as the backsheet 20, there can be employed a film which consists essentially of polyethylene, polypropylene or the like; an air ventilation resin film; or a sheet or the like obtained by bonding a ventilation resin film with a nonwoven cloth such as a spunbond or a spun lace. It is preferable that the backsheet 20 be made of a material having flexibility to an extent such that a sense of discomfort at the time of wearing does not occur. For example, it is preferable to use a film which consists essentially of a low density polyethylene (LDPE) resin, a total weight (weight per unit area: also referred to as a basis weight) of which is within the range of 15 $g/m^2$ to 30 $g/m^2$.

Next, the absorber 30 will be specifically described.

The absorber 30 includes a hydrophilic fiber or pulp. As examples of hydrophilic fibers, there can be employed solely or in combination: celluloses such as ground pulp or cotton; reproducible celluloses such as rayon or fibril rayon; semi-synthetic celluloses such as acetate or triacetate; particle-like polymers, fiber-like polymers, thermoplastic hydrophobic chemical fibers, or thermoplastic hydrophobic chemical fibers to which hydrophilic treatment is applied. Among them, it is preferable to use ground pulp in consideration of low cost and easiness of molding an absorber.

As the absorber 30, a mixture of a polymeric absorber with a hydrophilic film may be used. In the embodiment, the polymeric absorber is a grain-like polymer such as a sodium acrylate copolymer having absorptivity and hygroscopic property. The absorber 30 may be an air-raid sheet obtained by molding a hydrophilic fiber or powder in a sheet shape by means of an air-raid technique. In a case where the air-raid sheet is used as the absorber 30, it is preferable that a thickness of the air-raid sheet be 0.3 mm to 5.0 mm. As an example of air-raid sheet, there is employed the one obtained by molding a fiber and a grain-like polymer to be a sheet material by means of a binder or the like. The grain-like polymer may be dispersed in a layered shape or may be biased in a thickness direction in the air-raid sheet.

On the absorber 30, embosses may be appropriately formed in order to prevent deformation or folding while in wearing or to adjust a thickness. These embosses for the absorber 30 can be formed by passing the absorber between a patterned emboss roll and a flat roll. While the pattern for the emboss roll is formed in a lattice shape, in a dotted shape, or in a wavy shape, it is preferable to employ a lattice-shaped pattern which is easily adjusted in thickness.

The side sheets 41 and 42 will be described.

A material for the side sheets 41 and 42 can be selected from among similar materials which can be employed for the topsheet 10. It is preferable to have hydrophobic property or water repellent property in order to prevent menstrual blood from flowing over the side sheets 41 and 42 outward of the absorbent article 1 over the side sheets 41 and 42. Specifically, a spunbond nonwoven cloth, an SMS nonwoven cloth or the like is exemplified.

The side sheets 41 and 42 are arranged at both sides of the topsheet 10. The side sheet 41 covers a part of a side edge of the absorber 30 and the wing 61. One end part in a longitudinal direction of the side sheet 41 is a substantially straight line, and superimposes on one end part in a longitudinal direction of the topsheet 10. The other end part in the longitudinal direction of the side sheet 41 is coincident with a part of an outer circumference of the backsheet 20 and a shape of the wing portion 61. The side sheet 42 covers a part of a side edge of the absorber 30 and the wing portion 62. One end part in a longitudinal direction of the side sheet 42 is a substantially straight line, and superimposes on the other end part in the longitudinal direction of the topsheet 10. The other end part in the longitudinal direction of the side sheet 42 is coincident with a part of an outer circumference of the backsheet 20 and a shape of the wing portion 62.

The gathers 51 and 52 has a rubber 80 (not shown in FIG. 1, and refer to FIG. 2) as a member having elasticity. The gathers 51 and 52 are provided at both-side edges of the absorber 30. The gathers 51 and 52 are arranged along the longitudinal direction L of the absorbent article 1 in a state in which the rubber 80 is expanded. The gather 51 is bonded with the topsheet 10 at joint units 51f and 51r. The gather 52 is bonded with the topsheet 10 at joint units 52f and 52r.

An inside in the longitudinal direction L of the absorbent article 1 more than the joint units 51f and 51r of the gather 51 is not bonded with the topsheet 10. The gather 51 has end parts 51ff and 51rf of a free portion which is not bonded with the topsheet 10. The inside in the longitudinal direction of the absorbent article 1 more than the joint units 51f and 52r of the gather 51 is not bonded with the topsheet 10. The gather 52 has end parts 52ff and 52rf of a free portion which is not bonded with the topsheet 10.

In the absorbent article 1, the topsheet 10, the side sheets 41 and 42, the backsheet 20, and the absorber 30 are bonded with each other. Circumferential edges of the topsheet 10, the side sheets 41 and 42, and the backsheet 20 are bonded with each other, and the absorber 30 is internally sealed. As a method of bonding the topsheet 10 and the backsheet 20 with each other, it is possible to employ any one of heat emboss processing and ultrasonic or hot melt type adhesive agent or a combination of a plurality thereof.

Figure 2:
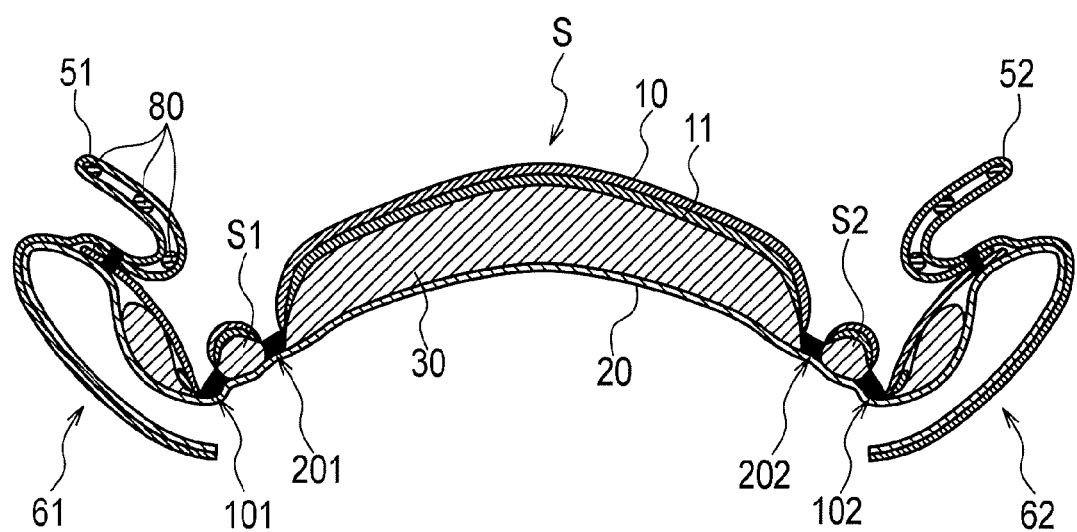
FIG. 2 is a sectional view taken along the line F1-F1' of the absorbent article of the first embodiment.

In the backsheet 20, on a surface coming into contact with shirt, an adhesive agent 70 is applied in a linear shape along a longitudinal direction of the backsheet 20 (not shown in FIG. 1, and refer to FIG. 2). The adhesive agent 70 is applied in a plurality of lines along the longitudinal direction of the backsheet 20. In each of the wing portion 61 and the wing portion 62, an adhesive agent is applied to a surface coming into contact with shirt as well. In a state before use, a protective sheet (not shown) for retaining stickiness is adhered as the adhesive agent 70. The protective sheet is released by a wearer when in use.

In the absorbent article 1 according to the embodiment, on a surface of the backsheet 10, first curved portions 101 and 102 and second curved portions 201 and 202 are formed along the longitudinal direction of the absorbent article 1.

The first curved portion 101 is an inside region more than both side parts 31 and 32 in a widthwise direction of the absorber 30 in planar view of the absorbent article 1, and is arranged in one pair symmetrical to a centerline CL of the absorbent article 1. The first curved portions 101 and 102 have a convex shape outward of the widthwise direction W of the absorbent article 1 in the middle region M including a contact region S in which a wearer's excretion part and the topsheet 10 come into contact with each other. The first curved portions 101 and 102 are formed to be thinner than a thickness of the absorbent article 1 in the contact region S in which the wearer's excretion part and the topsheet 10 come into contact with each other. In the embodiment, the first curved portions 101 and 102 are grooves that are formed in the topsheet 10.

The second curved portions 201 and 202 are formed along the longitudinal direction L of the absorbent article 1. The second curved portions 201 and 202 are arranged in one pair in an inside region in the widthwise direction W of the absorbent article 1 more than the first curved portions 101 and 102. The second curved portions 201 and 202 has a convex shape outward of the widthwise direction W of the absorbent article 1 in the middle region M including the contact region S in which the wearer's excretion part and the topsheet 10 come into contact with each other. The second curved portions 201 and 202 are formed to be thinner than a thickness of the absorbent article 1 in the contact region S in which the wearer's excretion part and the topsheet 10 come into contact with each other. In the embodiment, the second curved portions 201 and 202 are grooves that are formed in the topsheet 10.

The first curved portions 101 and 102 have middle wide portions 101a and 102a. At the middle wide portions 101a and 102a, an interval W0 between the first curved portions 101 and 102 is the widest.

The first curved portions 101 and 102 have forward narrow portions 101b and 102b which are forwarder than the middle wide portions 101a and 102a. At the forward narrow portions 101b and 102b, in a use state of the absorbent article 1, an interval W1 between the first curved portions 101 and 102 is narrower than that between the middle wide portions 101a and 102a. That is, an interrelationship of W0>W1 is established.

The first curved portions 101 and 102 have rearward narrow portions 101c and 102c which is more rearward than the middle wide portions 101a and 102a. At the rearward narrow portions 101c and 102c, in a use state of the absorbent article 1, an interval W2 between the first curved portions 101 and 102 is narrower than that between the middle wide portions 101a and 102a. That is, an interrelationship of W0>W2 is established.

Here, it is preferable that the interval W0 between the middle wide portions 101a and 102a be within the range of 20 mm to 60 mm. If the interval W0 is 20 mm or less, an absorption quantity in the middle region M cannot be ensured. If 60 mm is exceeded, an average crotch interval of a wearer is exceeded, thus imparting a sense of discomfort to a wearer.

FIG. 2 is a sectional view taken along the line F1-F1' of the absorbent article 1 shown in FIG. 1. FIG. 2 is also a sectional view when the absorbent article 1 is used. In FIG. 2, the wing portions 61 and 62 of the absorbent article 1 are folded to the side of the backsheet 20. As shown in FIG. 2, the rubber 80 is arranged at the gathers 51 and 52.

A basis weight of the absorber 30 that corresponds to the contact region S in which the wearer's excretion part and the topsheet 10 come into contact with each other is greater than that of an absorber that exists in a region S1 shown in FIG. 2 (between the first curved portion 101 and the second curved portion 201). Similarly, the basis weight of the absorber 30 is greater than that of an absorber that exists in a region S2 (between the first curved portions 102 and the second curved portion 202). For example, the basis weight of the absorber 30 is 500 g/m$^2$, and the basis weight of an absorber that exists in the region S1 (the basis weight of the absorber that exists in the region S2) is 200 g/m$^2$. In this manner, rigidity of a portion that corresponds to the contact region S of the absorbent article 1 is increased more than that in each of the regions S1 and S2.

Figure 3:
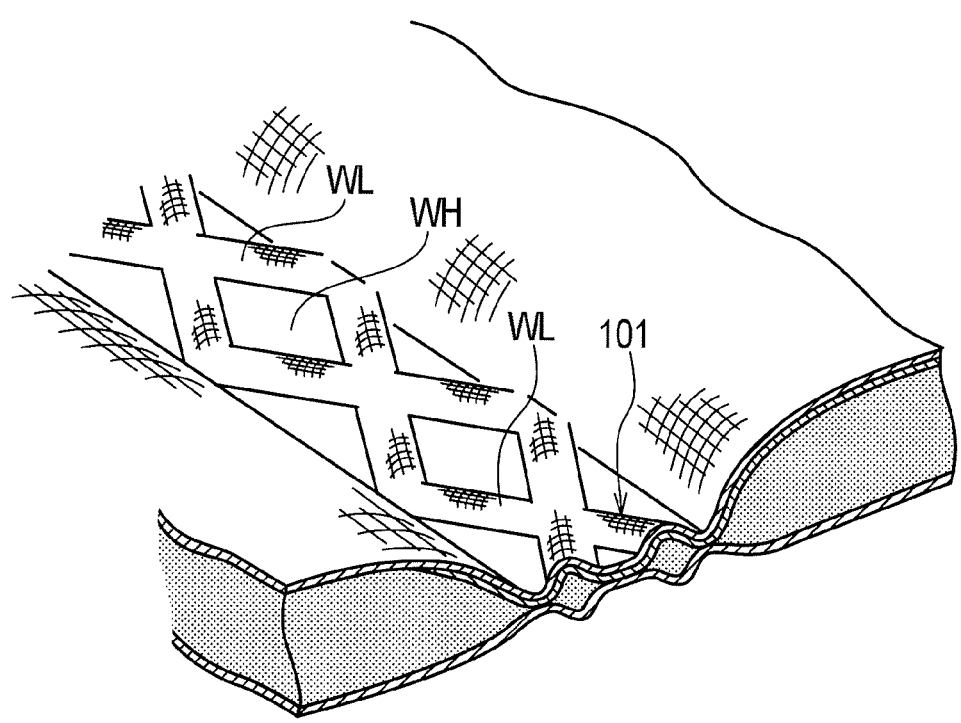
FIG. 3 is an enlarged view illustrating a first bending unit according to the first embodiment.

In the embodiment, the first curved portions 101 and 102 and the second curved portions 201 and 202 are formed by means of compression processing. FIG. 3 is an enlarged view of the first curved portion 101. The first curved portion 101 is formed to be thinner than a thickness of the absorbent article 1 in the contact region S in which the wearer's excretion part and the topsheet 10 come into contact with each other. The first curved portion 101 is a groove that is formed in the topsheet 10. A bottom part of the groove has: a high compression region WH in which density of the absorber 30 is increased by means of compression processing; and a low compression region WL in which the density is lower than that in the high compression region WH. In the embodiment, the low compression region WL is formed in a lattice shape. The absorbers opposed to each other via the first curved portion 101 are coupled with each other by means of the low compression region WL. It is preferable that a width W of the bottom part of the first curved portion 101 be within the range of 0.5 mm to 5 mm. If the width is 0.5 mm, rigidity of the bottom part cannot be ensured, and the bottom part may be severed. If 5 mm is exceeded, rigidity in a widthwise direction becomes too high, imparting a sense of discomfort to a wearer at the time of wearing. The first curved portion 102 and the second curved portions 201 and 202 also have a similar structure.

In the absorbent article 1, the middle wide portions 101a and 102a of the first curved portion 101 and the first curved portion 102 are formed in a convex shape outward in the widthwise direction W of the absorbent article 1 in planar view. Therefore, a femoral part H of a wearer easily comes into contact with the middle wide portions 101a and 102a of the absorbent article 1.

In addition, the first curved portions 101 and 102 and the second curved portions 201 and 202 are formed to be thinner than a thickness of the absorbent article 1 in the contact region S in which the wearer's excretion part and the topsheet 10 come into contact with each other; and therefore, the absorbent article 1 is easily bendable at the first curved portions 101 and 102 and the second curved portions 201 and 202.

Here, it is preferable that a basis weight of the absorber 30 at a portion that forms the first curved portions 101 and 102 and the second curved portions 201 and 202 be within the range of 100 g/m$^2$ to 450 g/m$^2$ in a state before compression processing. Alternately, it is preferable that a rigidity value of the absorber 30 that includes the first curved portions 101 and 102 and the second curved portions 201 and 202 be within the range of 500 mg to 2,500 mg (Galle rigidity value).

If the rigidity value is 500 mg or less, in a case where the absorbent article 1 is subjected to a force of orienting from both sides in the widthwise direction to the inside in the widthwise direction, it is impossible to ensure the rigidity of the bottom part of the first curved portions 101 and 102 and the second curved portions 201 and 202, and the bottom part may be bent or folded; and therefore, the absorbent article 1 may not be able to transmit the force of orienting from both sides in the widthwise direction to the inside in the widthwise direction into an extending direction of the first curved portions 101 and 102 and the second curved portions 201 and 202. In this case, an "action of deforming an absorbent article" to be described later hardly works.

Alternatively, if the rigidity value exceeds 2,500 mg, a following characteristic relative to a wearer's body lowers, easily imparting a sense of discomfort to a wearer.

When the absorbent article 1 is subjected to a force F of orienting to the inside in the widthwise direction, the absorbent article 1 bends to the side of the backsheet 20 while a portion (a groove bottom part) that is formed to be thin at the first curved portions 101 and 102 and the second curved portions 201 and 202 serves as a hinge. The region S1 between the first curved portion 101 and the second curved portion 201 and the region S2 between the first curved portion 101 and the second curved portion 202 get into the side of the backsheet 30 of the absorbent article 1, and support the middle region M in a direction approaching a wearer's skin. Therefore, an intimate contact property between the absorbent article 1 and the wearer can be increased.

In addition, an absorption surface of a body fluid in the topsheet 10 of the absorbent article 1 has the first curved portions 101 and 102 and the second curved portions 201 and 202 that are formed in a convex shape outward in the widthwise direction W; and therefore, even if a force is applied to the inside in the widthwise direction of the absorbent article 1 when in use, both side parts 31 and 32 of the absorber 30 are not narrowed. Therefore, this absorbent article 1 has an advantage that a sufficient absorption area is ensured in the middle region M of the absorbent article as well.

Hereinafter, an action of deforming the absorbent article will be described. The bottom part of the first curved portions 101 and 102 are compressed to thereby increase rigidity; and therefore, a force that is applied to the middle wide portions 101a and 102a to be oriented to the inside in the widthwise direction lifts the absorber 30 in a direction approaching a skin, and is transmitted along the first curved portions 101 and 102. As a result, this force acts in a direction of reducing an interval W1 between the forward narrow portions 101b and 102b and an interval W2 between the rearward narrow portions 101c and 102c.

The force of applying to the inside in the widthwise direction concentrates on the interval W1 between the forward narrow portions 101b and 102b and the intervals W2 between the rearward narrow portions 101c and 102c. At this time, the force of applying to the inside in the widthwise direction lifts the contact region S to the wearer's skin side. Further, the force F of applying to the middle wide portions 101a and 102a to be oriented to the inside in the widthwise direction extends the forward region F and the rearward region R to the outside in the widthwise direction of the absorbent article 1. The forward region F and the rearward region R are lifted in a direction approaching to the skin side while being subjected to this force. Thus, the forward region F and the rearward region R, are deformed in a cup shape while a space in the widthwise direction is ensured. Therefore, the contact region S comes into more intimate contact with the wearer's excretion part, making it possible to reliably receive the body fluid having flown into the forward region F and the rearward region R.

In addition, in the absorbent article 1, end parts of the first curved portions 101 and 102 (the forward narrow portions 101b and 102b and the rearward narrow portions 101c and 102c shown in the embodiment) are positioned inside in the widthwise direction of the absorbent article more than the middle wide portions 101a and 102a. Therefore, when in use, even if a body fluid gets into a space that is formed by the first curved portion 101, the second curved portion 202, and the region S1, shown in FIG. 2, in excess of an absorption surface of the topsheet 10, the body fluid is guided to the first curved portions 101 and 102 and then is flowed to the side of the absorber 30. Therefore, the leakage from the forward region F or the rearward region R of the absorbent article 1 can be prevented.

Further, at the first curved portions 101 and 102 and the second curved portions 201 and 202, of the absorbent article 1, the high compression region WH and the low compression region WL are formed by means of compression processing, and the low compression region WL is adapted to couple the absorbers 30 which is opposed to each other while the first curved portions are sandwiched therebetween. In the embodiment, the low compression region WL is formed at the bottom part of a groove, whereby the absorbers 30 are not divided to be separated from each other; and therefore, the absorption capacity is not lost. Accordingly, the absorbent article 1 is capable of increasing an intimate contact property between the absorbent article 1 and a wearer, and is also capable of reliably absorbing a body fluid.

(Second Embodiment)

Figure 4:
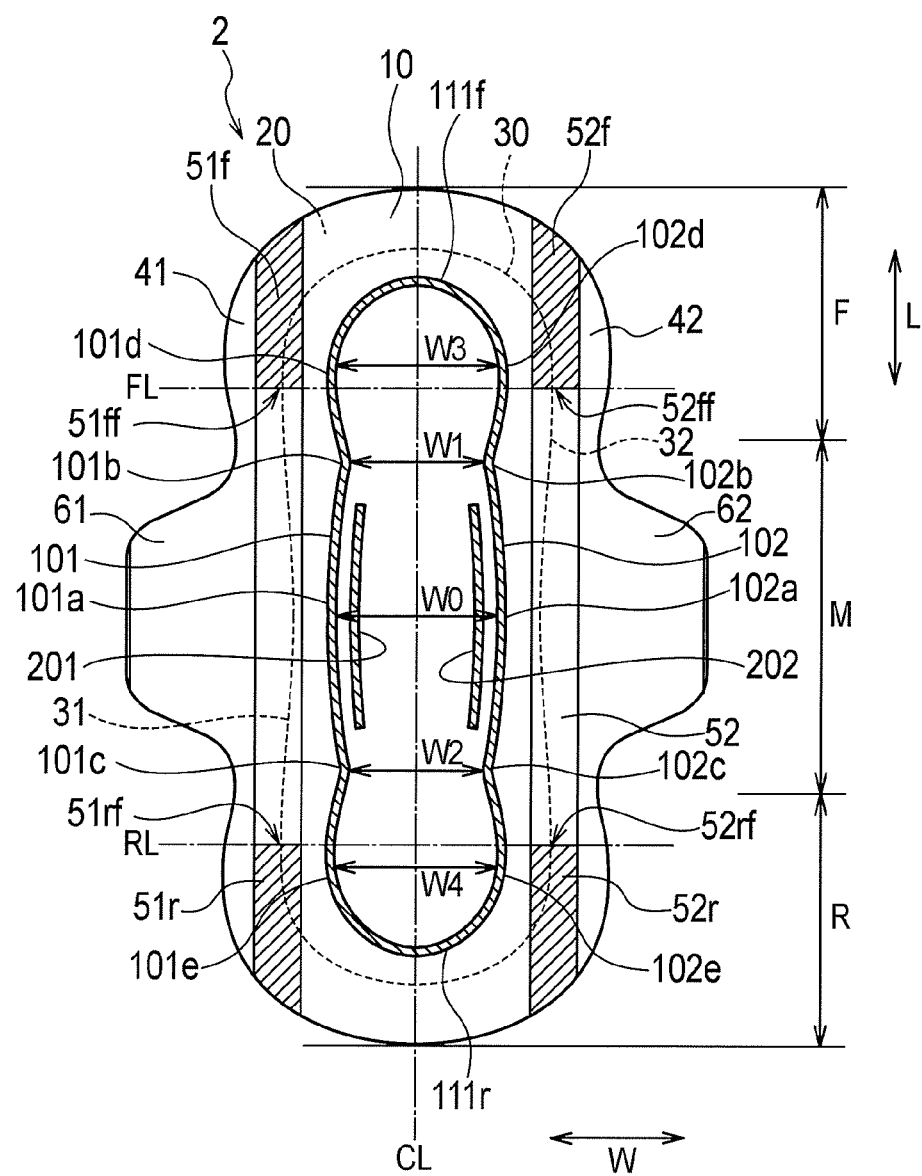
FIG. 4 is a plan view of an absorbent article according to a second embodiment.

A absorbent article 2 according to a second embodiment will be described with reference to FIG. 4. Like constituent elements in the absorbent article 1 shown in FIG. 1 are designated by like reference numerals, and a detailed description is omitted. In the absorbent article 2 shown in FIG. 4, the first curved portions 101 and 102 shown in FIG. 1 are extended in a longitudinal direction of the absorbent article. In addition, main transversely crossing curved portions 111f and 111r are formed in a forward region F and a rearward region R. The main transversely crossing curved portions 111f and 111r are formed to be thinner than a thickness of the absorbent article 1 in a contact region S in which a wearer's excretion part and a topsheet 10 come into contact with each other.

In the embodiment, the main transversely crossing curved portions 111f and 111r are grooves that are formed in the topsheet 10. At the main transversely crossing curved portion 111f and the man transversely curved portion 111r, like the first curved portions 101 and 102 and the second curved portions 201 and 202, a high compression region WH and a low compression region WL are formed by means of compression processing, and the low compression region WL is formed in a lattice shape.

In the absorbent article 2, the first curved portions 101 and 102 extends in a forward/backward direction more than end parts of the second curved portions 201 and 202 in a longitudinal direction of the absorbent article 2. The first curved portions 101 and 102 have middle wide portions 101a and 102a. At the middle wide portions 101a and 102a, an interval W0 between the first curved portions 101 and 102 is the widest.

The first curved portions 101 and 102 have forward narrow portions 101b and 102b forwarder than the middle wide portions 101a and 102b. At the forward narrow portions 101b and 102b, in a use state of the absorbent article 2, an interval W1 between the first curved portions 101 and 102 is narrower than that between the middle wide portions 101a and 102a. That is, an interrelationship of W0>W1 is established.

The first curved portions 101 and 102 have rearward narrow portions 101ac and 102c more rearward than the middle wide portions 101a and 102a. At the rearward narrow portions 101c and 102c, in a use state of the absorbent article 2, an interval W2 between the first curved portions 101 and 102 is narrower than that between the middle wide portions 101a and 102a. That is, an interrelationship of W0>W2 is established.

The first curved portions 101 and 102 have forward wide portions 101d and 102d which are further forwarder than the forward narrow portions 101b and 102b. At the forward wide portions 101d and 102d, in a use state of the absorbent article 2, an interval W3 between the first curved portions 101 and 102 is wider than that between the forward narrow portions 101b and 102b. That is, an interrelationship of W3>W1 is established.

The first curved portions 101 and 102 have rearward wide portions 101e and 102e more rearward than the rearward narrow portions 101c and 102c. At the rearward wide portions 101e and 102e, in a use state of the absorbent article 2, an interval W4 between the first curved portions 101 and 102 is wider than that between the rearward narrow portions 101c and 102c. That is, an interrelationship of W4>W2 is established.

Here, it is preferable that the interval W0 between the middle wide portions 101a and 102a be within the range of 20 mm to 60 mm. If the interval W0 is 20 mm or less, an absorption quantity in the middle region M cannot be ensured. If 60 mm is exceeded, an average crotch interval of a wearer is exceeded, thus imparting a sense of discomfort to the wearer.

The absorbent article 2 has a main transversely crossing curved portion 111f that extends in a widthwise direction of the absorbent article 2 between the forward wide portions 101d and 102d. The main transversely crossing curved portion 111f is formed in a curved shape having a convex shape in a forward direction. Both end parts in a widthwise direction of the main transversely crossing curved portion 111f are coupled with forward end parts of the curved portions 101 and 102.

In addition, the absorbent article 2 has a main transversely crossing curved portion 111r that extends in a widthwise direction of the absorbent article 2 between the rearward wide portions 101e and 102e. The main transverse crossing curved portions 111r is formed in a curved shape having a convex shape in a rearward direction. Both end parts in a widthwise direction of the main transversely crossing curved portion 111r are coupled with rearward end parts of the first curved portions 101 and 102.

A virtual line FL, which is adapted to connect an end part 51ff of a free portion of a gather 51 and an end part 52ff of a free portion of a gather 52 to each other, and one pair of first curved portions 101 and 102, are adapted to cross each other.

A virtual line RL, which is adapted to connect an end part 51rf of a free portion of the gather 51 and an end part 52rf of a free portion of the gather 52 to each other, and one pair of first curved portions 101 and 102, are adapted to cross each other.

Figure 5:
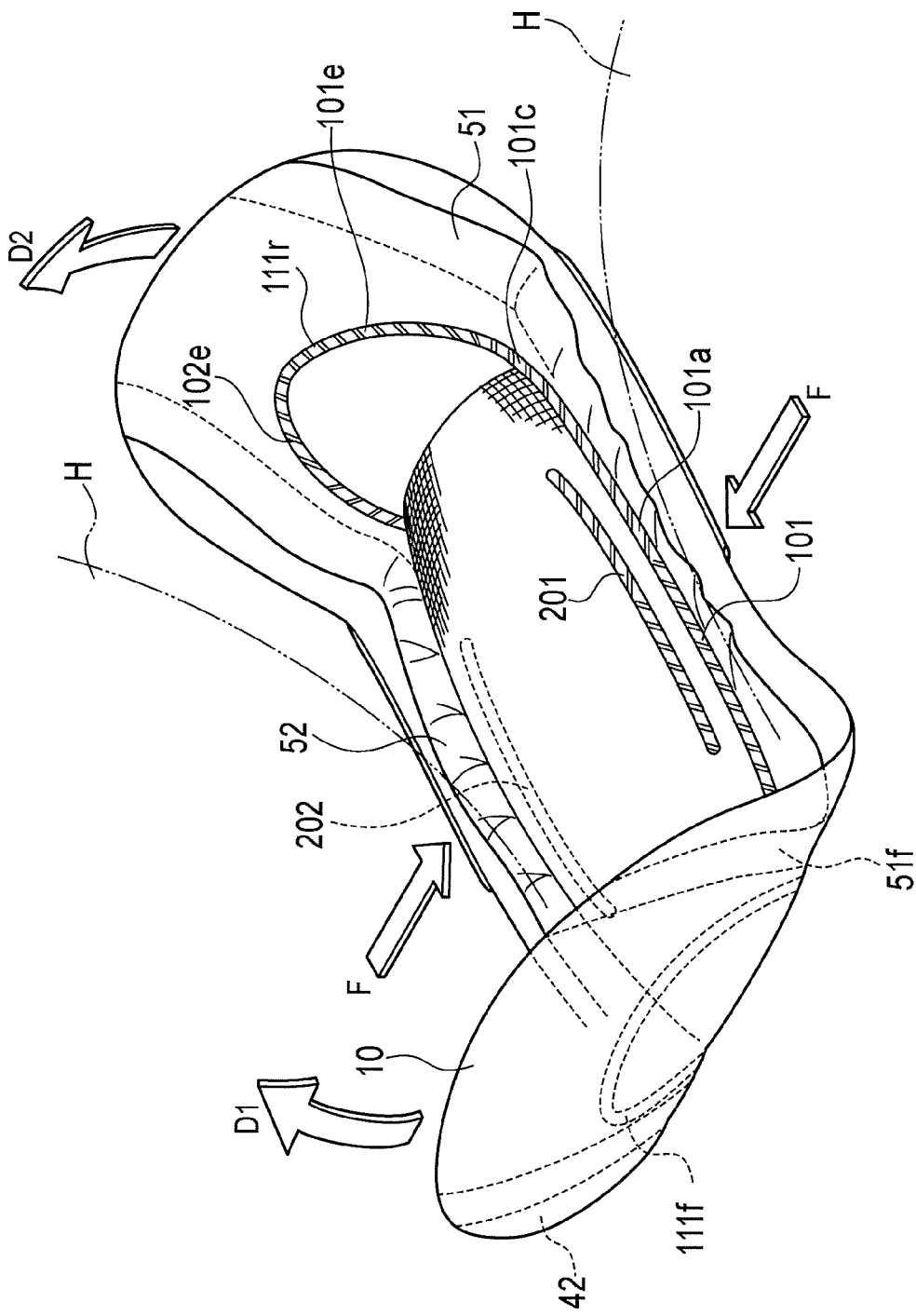
FIG. 5 is a schematic view illustrating a shape at the time of wearing the absorbent article according to the second embodiment.

FIG. 5 is a schematic view illustrating a shape at the time of wearing the absorbent article 2 according to the embodiment. In the absorbent article 2, the middle wide portions 101a and 102a of the first curved portions 101 and the first curved portion 102 are formed in a convex shape outward in the widthwise direction W of the absorbent article 2 in planar view. Thus, a femoral part H of a wearer easily comes into contact with the middle wide portions 101a and 102a of the absorbent article 2.

In addition, the first curved portions 101 and 102 and the second curved portions 201 and 202 are formed to be thinner than a thickness of the absorbent article 1 in the contact region S in which the wearer's excretion part and the topsheet 10 come into contact with each other; and therefore, the absorbent article 1 is easily bendable at the first curved portions 101 and 102 and the second curved portions 201 and 202.

When the absorbent article 1 is subjected to a force F of orienting to the inside in the widthwise direction, the absorbent article 1 bends to the side of the backsheet 20 while a portion (a bottom part of a groove) formed to be thin at the first curved portions 101 and 102 and the second curved portions 201 and 202 serves as a hinge. A region S1 between the first curved portion 101 and the second curved portion 201 and a region S2 between the first curved portion 101 and the second curved portion 202 get into the side of the backsheet 30 of the absorbent article 1, and support a middle region M in a direction approaching a wearer's skin. Therefore, an intimate contact property between the absorbent article 1 and the wearer can be increased.

In addition, a bottom part of the first curved portions 101 and 102 is compressed to thereby increase rigidity; and therefore, a force F that is applied to the middle wide portions 101a and 102a to be oriented to the inside in the widthwise direction lifts the absorber 30 in a direction approaching to a skin, and is transmitted along the first curbed portions 101 and 102. As a result, this force acts in a direction of reducing the intervals W1 between the forward narrow portions 101b and 102b and the interval W2 between the rearward narrow portions 101c and 102c.

The force F that is applied to the inside in the widthwise direction concentrates on the interval W1 between the forward narrow portions 101b and 102b and the interval W2 between the rearward narrow portions 101c and 102c. At this time, the force applied to the inside in the widthwise direction lifts the contact region S to the wearer's skin side. Further, the force F that is applied to the middle wide portions 101a and 102a to be oriented to the inside in the widthwise direction transmits the forward wide portions 101d and 102d and the rearward wide portions 101e and 102e, and extents the forward region F and the rearward region R to the outside in the widthwise direction of the absorbent article 2. The forward region F and the rearward region R, are pulled up in directions D1 and D2 approaching to a skin side while being subjected to this force. Thus, the forward region F and the rearward region R, are deformed in a cup shape while a space in the widthwise direction is ensured. Therefore, the contact region S comes into more intimate contact with the wearer's excretion part, making it possible to reliably receive the body fluid having flown into the forward region F and the rearward region R.

The absorbent article 2 has the main transversely crossing curved portions 111f and 111r, whereby rigidity in the longitudinal direction is weakened, and thus, the absorbent article is easily bendable in the longitudinal direction. Therefore, when the force F is applied so that the absorbent article 2 is compressed to the inside in the widthwise direction of the absorbent article 2, the forward wide portions 101d and 102d and the rearward wide portions 101e and 102e are easily pulled toward the skin side, and is easily deformable in a cup shape.

In addition, an absorption surface of a body fluid in the topsheet 10 of the absorbent article 2 has the first curved portions 101 and 102 and the second curved portions 201 and 202 that are formed in a convex shape outward in the widthwise direction W. Thus, even if the force F is applied to the inside in the widthwise direction of the absorbent article 2 when in use, the absorbent article 2 curves along the first curved portions 101 and 102 and the second curved portions 201 an 202, thereby preventing an occurrence of wrinkles expending in the longitudinal direction at a part of the absorber 30 that is positioned between the forward wide portions 101d and 102d and the rearward wide portions 101e and 102e or preventing an occurrence of folding in the longitudinal direction. That is, it is possible to prevent an unnecessary force from being applied to the absorber 30. In this manner, both side parts 31 and 32 of the absorber 30 are never narrowed. Therefore, the absorbent article 2 also has an advantage that a sufficient absorption area is ensured in the middle region M of the absorbent article 2.

Further, in the absorbent article 2, the forward narrow portions 101b and 102b and the rearward narrow portions 101c and 102c are positioned inside in the widthwise direction of the absorbent article more than the middle wide portions 101a and 102a. Thus, when in use, even in a case where a body fluid gets into a space that is formed by the first curved portion 101, the second curved portion 202, and the region S1 shown in FIG. 2, in excess of the absorption surface of the topsheet 10, the body fluid is guided to the first curved portions 101 and 102 and then is flowed to the side of the absorber 30. Therefore, the leakage from the forward region F or the rearward region R of the absorbent article 2 can be prevented.

Furthermore, at the first curved portions 101 and 102 and the second curved portions 201 and 202, of the absorbent article 2, the high compression region WH and the low compression region WL are formed by means of compression processing, and the low compression region WL is adapted to couple the absorbers 30 that are opposed to each other while the absorbers and the first curved portions are sandwiched therebetween. In the embodiment, the absorbers 30 are not divided to be separated from each other by means of the low compression region WL that is formed at the bottom part of a groove, and thus, an absorption capacity is not lost. Therefore, the absorbent article 2 is capable of increasing an intimate contact property between the absorbent article 2 and a wearer and is capable of reliably absorbing a body fluid.

(Third Embodiment)

Figure 6:
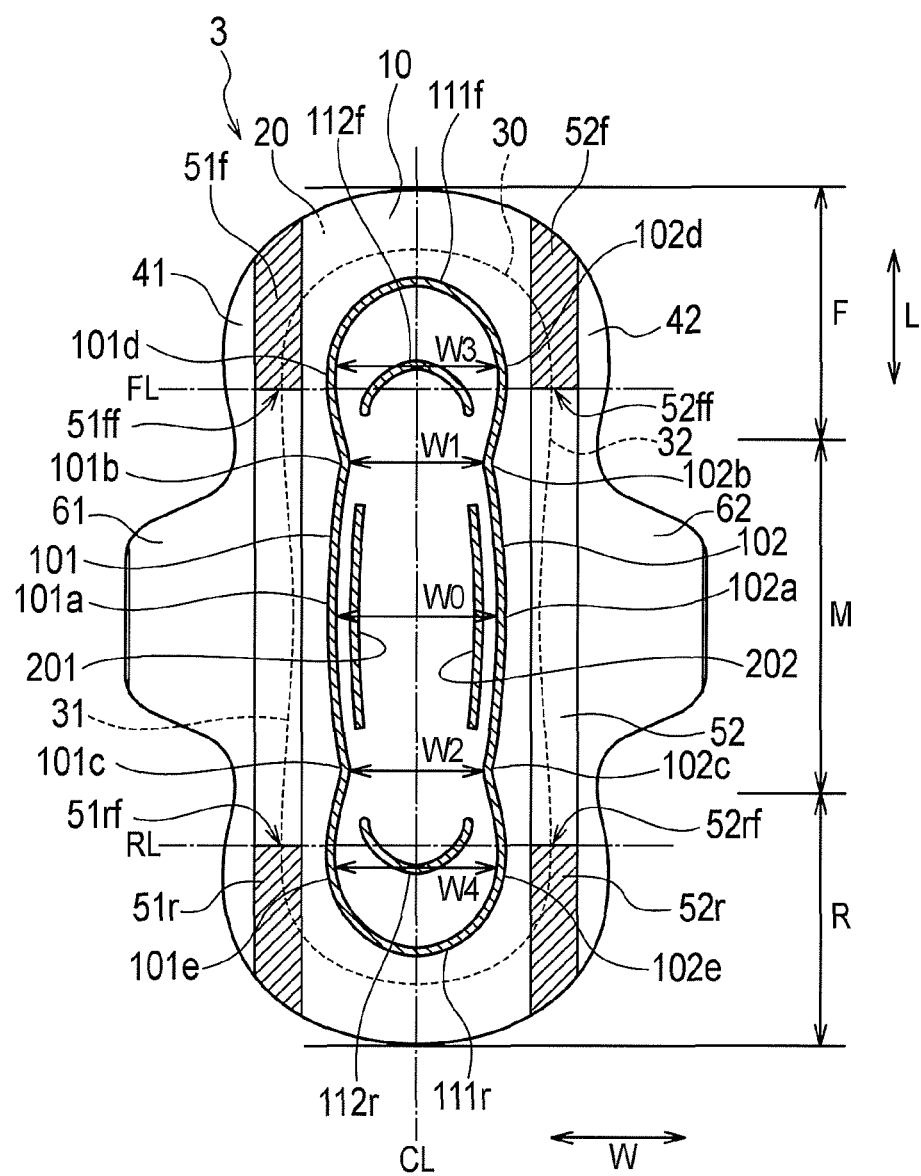
FIG. 6 is a plan view of an absorbent article according to a third embodiment.

An absorbent article 3 according to a third embodiment will be described with reference to FIG. 6. Like constituent elements in the absorbent articles 1 and 2 described above are designated by same reference numerals, and a detailed description is omitted. In the absorbent article 3 shown in FIG. 6, the first curved portions 101 and 102 shown in FIG. 1 are extended in a longitudinal direction of the absorbent article. In addition, main transversely crossing curved portions 111f and 111r are formed in a forward region F and a rearward region R. Further, subsidiary transversely crossing curved portions 112f and 112r are formed. The subsidiary transversely crossing curved portions 112f and 112r are formed to be thinner than a thickness of the absorbent article 1 in a contact region S in which a wearer's excretion part and a surface sheet 10 come into contact with each other. In the embodiment, the subsidiary transversely crossing curved portions 112f and 112r are grooves that are formed in the surface sheet 10.

In the embodiment, in the subsidiary transversely crossing curved portions 112f and 112r, like the first curved portions 101 and 102 and the second curved portions 201 and 202, a high compression region WH and a low compression region WL are formed by means of compression processing, and the low compression region WL is formed in a lattice shape.

In the absorbent article 3 according to the embodiment, the first curved portions 101 and 102 and the second curved portions 201 and 202 are formed along a longitudinal direction of the absorbent article 3 on the surface of the surface sheet 10. Intervals between the first curved portions 101 and 102 in middle wide portions 101a and 102a, forward narrow portions 101b and 102b, rearward narrow portions 101c and 102c, and rearward wide portions 101e and 102e are identical to those in the second embodiment.

The absorbent article 3 has the subsidiary transversely crossing curved portions 112f and 112r. The subsidiary transversely crossing curved portion 112f is formed at the side of a middle region M more than the main transversely crossing curved portion 111f. The subsidiary transversely crossing curved portion 112f is formed in a curved shape having a convex shape in a forward direction. The subsidiary transversely crossing curved portion 112r is formed at the side of the middle region M more than the main transversely crossing curved portion 111r. The subsidiary transversely crossing curved portion 112r is formed in a curved shape having a convex shape in a rearward direction.

A virtual line FL, which is adapted to connected an end part 51ff of a free portion of a gather 51 and an end part 52ff of a free portion of a gather 52 to each other, and one pair of first curved portions 101 and 102 are adapted to cross each other. In addition, the virtual line FL is adapted to cross the subsidiary transversely crossing curved portion 112f.

A virtual line RL, which is adapted to connected an end part 51rf of a free portion of a gather 51 and an end part 52rf of a free portion of a gather 52 to each other, and one pair of first curved portions 101 and 102 are adapted to cross each other. In addition, the virtual line RL is adapted to cross the subsidiary transversely crossing curved portion 112r.

As described above, the absorbent article 3 has the main transversely crossing curved portions 111f and 111r and the subsidiary transversely crossing curved portions 112f and 112r, whereby a portion at which rigidity in a longitudinal direction is weakened increases, and thus, the absorbent article is bendable more easily in the longitudinal direction.

Therefore, the forward wide portions 101*d* and 102*d* and the rearward wide portions 101*e* and 102*e* are pulled toward a skin side more easily by means of a force F that is applied so that the absorbent article 3 is compressed to the inside in the widthwise direction of the absorbent article 3, and then, deformation into a cup shape is accelerated.

In addition, since an absorption surface of a body fluid in the topsheet 10 of the absorbent article 3 has the first curved portions 101 and 102 and the second curved portions 201 and 202 that are formed in a convex shape outward in a widthwise direction W, even if the force F is applied to the inside in the widthwise direction of the absorbent article 3 when in use, both side parts 31 and 32 of an absorber 30 are not narrowed. Therefore, the absorbent article 3 also has an advantage that a sufficient absorption area is ensured in the middle region M of the absorbent article 3.

Further, in the absorbent article 3, the forward narrow portions 101*b* and 102*b* and the rearward narrow portions 101*c* and 102*c* are positioned inside in the widthwise direction of the absorbent article more than the middle wide portions 101*a* and 102*a*. Therefore, when in use, even in a case where a body fluid gets into a space that is formed by the first curved portion 101, the second curved portion 202, and the region S1, shown in FIG. 2, in excess of the absorption surface of the topsheet 10, the body fluid is guided to the first curved portions 101 and 102 and then is flowed to the side of the absorber 30. Therefore, the leakage from the forward region F or the rearward region R of the absorbent article 3 can be prevented.

Furthermore, at the first curved portions 101 and 102 and the second curved portions 201 and 202, of the absorbent article 3, the high compression region WH and the low compression region WL are formed by means of compression processing, and the low compression region WL is adapted to couple the absorbers 30 that are opposed to each other while the absorbers and the first curved portions are sandwiched therebetween. In the embodiment, the low compression region. WL is formed at the bottom part of a groove, whereby the absorbers 30 are not divided to be separated from each other; and therefore, the absorption capacity is not lost. Therefore, the absorbent article 3 is capable of increasing an intimate contact property between the absorbent article 3 and a wearer, and is also capable of reliably absorbing a body fluid.

(Other Embodiments)

As described above, while the contents of the present invention were disclosed through the first to fourth embodiments, it should not be understood that the discussion and drawings forming a part of this disclosure limit the present invention. From this disclosure, a variety of substitute embodiments, examples, and operational techniques would have been self-evident to one skilled in the art.

The embodiments can be modified as follows. While the foregoing embodiments described that the absorbent article is a sanitary napkin, the embodiments can be applied to a so called liner or an incontinence article (referred to as an incontinence pad) or the like.

The absorbent article is not limitative to the planar shape disclosed in FIG. 1 described above. The absorbent article may be formed in a shape conforming to a shape of a wearer's crotch and a shape of shirt. A planer shape of the absorbent article can be formed in a variety of shapes such as a rectangular shape, an elliptical shape, or a gourd shape.

The embodiments described that, at the first curved portions 101 and 102, the second curved portions 201 and 202, the main transversely crossing curved portions 111*f* and 111*r*, and the subsidiary transversely crossing curved portions 112*f* and 112*r*, the high compression region WH in which density of the absorber 30 is increased and the low compression region WL in which the density is lower than that in the high compression region WH are formed in a lattice shape.

However, a pattern, which is formed by compression at the first curved portions 101 and 102, the second curved portions 201 and 202, the main transversely crossing curved portions 111*f* and 111*r*, and the subsidiary transversely crossing curved portions 112*f* and 112*r*, is not limitative to the lattice shape. For example, a dot shape, a wavy shape, a shaded shape or the like is employed. The rigidity in the longitudinal direction or widthwise direction of the absorbent article can be varied by varying the shape in the low compression region and the high compression shape. Therefore, for example, an absorbent article having a basis weight of the absorber 30, which is greater than that of each of the absorbent articles that were illustrated in the embodiments, is of such a type that a low compression region is formed in a ladder shape (a shaded shape), (that is, a continuous low compression region is not formed in a longitudinal direction), whereby rigidity of the absorbent article in which the rigidity in the longitudinal direction is likely to be high can be lowered.

As described above, of course, the present invention includes a variety of embodiments or the like, which are not described herein. Therefore, a technical scope of the present invention is defined by only the specific matters of the invention according to the claims that are reasonable from the foregoing description.

The whole contents of JP-A-2009-096525 (filed in Apr. 10, 2009) are incorporated in the present specification by reference.

Industrial Applicability

According to the present invention, an intimate contact property with a wearer's excretion part can be increased, and a body fluid can be reliably absorbed.

The invention claimed is:

1. An absorbent article, comprising:
a topsheet having a contact surface configured to come into contact with a skin of a wearer;
a liquid-impermeable backsheet;
an absorber arranged between the topsheet and the backsheet and including absorbing material; and
a pair of leakage prevention units arranged at positions corresponding to both side parts of the absorber in a planar view of the absorbent article,
wherein
the absorbent article further includes a pair of first curved portions and a pair of second curved portions,
the first curved portions and second curved portions are thinner than a thickness of the absorbent article in a contact region configured to come into contact with an excretion part of the wearer,
the first curved portion are symmetrical to each other about a centerline of the absorbent article, are arranged between the side parts of the absorber in a widthwise direction of the absorbent article, and extend along a longitudinal direction of the absorbent article,
the second curved portions are arranged between the first curved portions in the widthwise direction of the absorbent article, and extend along the longitudinal direction of the absorbent article,
the contact region is arranged between the second curved portions,
each of the first curved portions and the second curved portions has a convex shape outward in the widthwise direction of the absorbent article, the first curved portions and the second curved portions are compressed, at least each of the first curved portions includes
a high compression region;
a low compression region having a density of the absorbing material lower than that in the high compression region, wherein the absorbing material on opposite sides of the first curved portion are connected with each other by the low compression region;
a middle wide portion in which an interval between the first curved portions is the widest in the widthwise direction of the absorbent article;
a forward narrow portion in which the interval between the first curved portions in the widthwise direction is narrower than that in the middle wide portion, the forward narrow portion being forward of the middle wide portion in the longitudinal direction;
a rearward narrow portion in which the interval between the first curved portions in the widthwise direction is narrower than that in the middle wide portion, the rearward narrow portion being rearward of the middle wide portion in the longitudinal direction;
a forward wide portion in which the interval between the first curved portions in the widthwise direction is wider than that in the forward narrow portion, the forward wide portion being forward of the forward narrow portion in the longitudinal direction; and
a rearward wide portion in which the interval between the first curved portions in the widthwise direction is wider than that in the rearward narrow portion, the rearward wide portion being rearward of the rearward narrow portion in the longitudinal direction, the absorbent article further comprises
a main transversely crossing curved portion extending in the widthwise direction and arranged between the forward wide portions or between the rearward wide portions of the first curved portions, and
at least one subsidiary transversely crossing curved portion extending in the widthwise direction and arranged between the middle wide portions and the main transversely crossing curved portion, the pair of first curved portions is configured to cross a virtual line which is parallel to the widthwise direction and connects end parts of joint units where the pair of the leakage prevention units is bonded to the topsheet, the main transversely crossing curved portion or the subsidiary transversely crossing curved portion is configured to cross the virtual line, and a width of a bottom part of each of the first curved portions is within a range of 0.5 mm to 5 mm.

2. The absorbent article according to claim 1, wherein a basis weight of the absorbing material that exists at a position corresponding to the contact region is greater than a basis weight of the absorbing material that exists between the first curved portions and the second curved portions.

* * * * *